United States Patent [19]

Schröder et al.

[11] Patent Number: 4,501,726

[45] Date of Patent: Feb. 26, 1985

[54] INTRAVASCULARLY ADMINISTRABLE, MAGNETICALLY RESPONSIVE NANOSPHERE OR NANOPARTICLE, A PROCESS FOR THE PRODUCTION THEREOF, AND THE USE THEREOF

[76] Inventors: Ulf Schröder, Fagottgränden 11 B, S-223 68 Lund; Klaus Mosbach, Lackalänga 31, S-244 02 Furulund, both of Sweden

[21] Appl. No.: 522,159

[22] PCT Filed: Nov. 11, 1982

[86] PCT No.: PCT/SE82/00381
§ 371 Date: Jul. 8, 1983
§ 102(e) Date: Jul. 8, 1983

[87] PCT Pub. No.: WO83/01738
PCT Pub. Date: May 26, 1983

[30] Foreign Application Priority Data

Nov. 12, 1981 [SE] Sweden ............................ 8106723

[51] Int. Cl.$^3$ .................................................. B01J 13/02
[52] U.S. Cl. ................................... 424/1.1; 128/1.3; 604/890
[58] Field of Search .................... 424/1.1, 19–25; 128/1.3; 604/890, 894; 252/62.53, 62.54, 316

[56] References Cited

U.S. PATENT DOCUMENTS

| | | | |
|---|---|---|---|
| 4,247,406 | 1/1981 | Widder et al. | 424/1.1 |
| 4,331,654 | 5/1982 | Morris | 128/1.3 |
| 4,345,588 | 8/1982 | Widder et al. | 128/1.3 |
| 4,357,259 | 11/1982 | Senyei et al. | 424/1.1 |

FOREIGN PATENT DOCUMENTS

| | | |
|---|---|---|
| 0021009 | 7/1981 | European Pat. Off. |
| 1021330 | 7/1981 | European Pat. Off. |

OTHER PUBLICATIONS

Abstract: Japanese Pat. No. 52-136911; K. Tateishi.
Abstract: Japanese Pat. No. 55-57516; M. Hasegawa.
Abstract: Japanese Pat. No. 55-47615; K. Oshira.

*Primary Examiner*—Ben R. Padgett
*Assistant Examiner*—T. J. Wallen
*Attorney, Agent, or Firm*—Merchant, Gould, Smith, Edell, Welter & Schmidt

[57] ABSTRACT

An intravascularly administrable, magnetically responsive nanosphere or nanoparticle made up of a crystalline carbohydrate matrix, preferably starch, enclosing a magnetic material, is described. The nanosphere or nanoparticle is produced by dissolving a carbohydrate together with a magnetic material to form a solution which is emulsified in a hydrophobic solvent from which the carbohydrate is crystallized.

The resulting magnetic nanospheres having an average diameter not exceeding 1500 nm are capable of transporting pharmacologically active substances and can be injected intravenously for subsequent concentration in a part of the body by means of a magnetic field.

8 Claims, No Drawings

INTRAVASCULARLY ADMINISTRABLE, MAGNETICALLY RESPONSIVE NANOSPHERE OR NANOPARTICLE, A PROCESS FOR THE PRODUCTION THEREOF, AND THE USE THEREOF

The present invention relates to a magnetically responsive and biologically degradable nanosphere or nanoparticle for intravascular administration, to a process for the production thereof, and to the use thereof for the transport and concentration of pharmaceuticals.

BACKGROUND

It has long been desired, in the treatment of different diseases, to be able specifically to deliver a pharmaceutical to a particular spot in the body, in particular in the treatment of tumours because of the grave systemic secondary effects produced by cytostatics. Various chemical methods have been tested in which it was tried to utilize differences in cell structure between tumour cells and healthy cells. However, no such test has been shown to give unequivocal results, above all because the difference between the tumour cells and the healthy cells is so insignificant.

One way of solving this problem is to utilize magnetic carriers of pharmaceuticals which are injected into the blood-vessel system and transported by the blood to be stopped at the target by means of a magnetic field.

U.S. Pat. No. 4,335,094 (priority June 2, 1977) discloses microspheres containing magnetic material incorporated with a polymer which, in addition, carries biologically active components.

U.S. Pat. No. 4,247,406 contains a detailed description of the use and production of magnetic microspheres made up of a magnetic material which has been enclosed in a polymer consisting of albumin.

One highly important reason for enclosing the magnetic material in a matrix, and for not using only the magnetic material, is that a matrix makes it possible to transport greater amounts of pharmalogically active substance per microsphere or microparticle, which is a prior condition of opening up possibilities of providing therapeutical concentrations of the pharmacologically active substances at the target site, without increasing the number of microspheres to such an extent that the capillaries are occluded. The requirements placed on the matrix used in such contexts are as follows:

1. The matrix should in itself be chemically inert in biological systems.
2. The matrix should be biologically well-characterised.
3. The matrix should be non-toxic and non-immunogenic.
4. The matrix should be dischargeable from the body via normal routes.
5. The matrix preparation should be readily administrable.
6. The matrix preparation should be able to release a biologically active substance, and the release rate of the active substance should be readily controllable.
7. The matrix should be usable for enclosing and releasing substances having different molecular weights.

In addition to polymers of amino acids, such as albumin, carbohydrates are conceivable. Starch and glycogen are such carbohydrates made up of glucose units and satisfying the requirements for biocompatibility, primarily because they are the body's own substances, which means that secondary effects in the form of hypersensitivity reactions are avoided. The body's own enzyme for degrading starch is alpha-amylase which specifically degrades alpha(1–4) bonds.

The use of starch is disclosed by DE-OS No. 25 24 278 which describes the preparation and utilization of covalent cross-linked microspheres of starch having a size so selected that the microspheres will get caught in the capillaries and thereby can be utilized as a diagnostic means in the vascular system. To ensure that these microspheres get caught, the size of the microsphere must be above 10 $\mu$m.

To enable a microsphere injected into the vascular system to circulate, the diameter of the microsphere must be below 1 $\mu$m. This has been shown by, inter alia, Okamoto et al (Chem. Pharm. Bull. (1975) 23(7), 1452–1457) who also have shown that the surface structure must be hydrophilic. The magnetic albumin microspheres previously mentioned are hydrophobic and cannot therefore circulate, but must be injected arterially towards the target site.

The present specification describes a simple and reproducible process for the production of magnetically responsive crystalline nanospheres or nanoparticles for the concentration of pharmaceuticals.

DESCRIPTION OF THE INVENTION

The present invention provides a magnetically responsive and biologically degradable nanosphere or nanoparticle for intravascular administration, which is made up of a matrix in which a magnetic material is enclosed. The nanosphere or nanoparticle is characterised in that its average diameter does not exceed 1500 nm, and preferably is less than 1000 nm, and in that the matrix is a crystalline carbohydrate.

Carbohydrate polymers containing alpha(1–4) bonds are especially useful because they can be degraded by the alpha-amylase in the body. Although starch is preferred, also pullullan, glycogen and dextran may be used. It is also possible to modify the carbohydrate polymer with, for example, hydroxyethyl, hydroxypropyl, acetyl, propionyl, hydroxypropanoyl, various derivatives of acrylic acid or like substituents.

Also carbohydrates which are not polymeric, may be used in the context of this invention. Examples of such carbohydrates are glucose, maltose and lactose.

Pharmaceuticals may be adsorbed to the carbohydrates after the nanosphere has been produced. This may be important in such cases where the pharmaceutical in question is damaged by the treatment in connection with the production of the magnetic nanospheres. If the matrix is a carbohydrate, it is also possible to modify the matrix by covalently coupling to the carbohydrate e.g. amino groups or carboxylic acid groups, thereby to create an adsorption matrix. High molecular substances of the type proteins may be enclosed within the matrix for later release.

The invention also comprises a process for the production of magnetic nanospheres having a diameter below 1.5 $\mu$m. The process is characterised in that a carbohydrate is dissolved in a solvent having a high dielectric constant to form a clear solution. To this solution, the magnetic material is added, whereupon the hydrophilic solution is emulsified in a hydrophobic solvent. The resulting emulsion is stabilized by supplying thereto a stabilizing medium, or by transferring the emulsion to such a medium, whereby the carbohydrate is crystallized, while enclosing the magnetic material, to magnetic nanospheres or nanoparticles having an average diameter which does not exceed 1500 nm and preferably is less than 1000 nm.

The carbohydrate is dissolved in a concentration which varies from one solvent to another but which normally lies within the range 5-250% (weight volume). Conceivable such solvents are, inter alia, dimethyl formamide, ethylene glycol, sulpholane, dimethyl sulphoxide, propylene carbonate, water and formamide, or mixtures thereof.

The magnetic material may consist of magnetic magnetite particles ($Fe_3O_4$) having a size of 10-20 nm. One process for the production of such small particles is known, and the particles are commercially available from Ferrofluid Corp., USA. Other useful magnetic materials include particles or colloids having a substantial content of the aluminium, nickel, cobalt, copper, silver, manganese, or platinum.

The amount of magnetic particles in the magnetic nanospheres may vary within wide limits. In actual practice, however, the range is rather narrow, and preferably use is made of 10-150 parts by weight of magnetic particles per 100 parts by weight of matrix. The mixture of the dissolved carbohydrate and the magnetic material is emulsified in a hydrophobic phase, resulting in the formation of a W/O emulsion. The hydrophobic phase employed may be a vegetable oil, preferably maize oil, or an organic solvent in which one or more emulsifiers have been dissolved. Among such useful organic solvents are, inter alia, xylene, toluene, ethyl benzene, diethyl benzene, propyl benzene, ethylene chloride and the like, as well as mixtures thereof. The emulsification system which has been found to give the best results, consists of the solvents xylene/$CHCl_3$ (4:1) in which the emulsifiers Pluronic F-68 ® and Pluronic L-35 ® have been dissolved to a concentration of 2.5% (weight volume) of each emulsifier.

To emulsify the suspension Sonicator or a high-pressure homogenizer is used. The resulting emulsion in which the matrix with the magnetic material is suspended in the form of droplets having a maximum size of 2 μm, is stabilized by transferring it to a liquid capable of crystallizing the carbohydrate, whereby the magnetic material will be enclosed. Examples of such liquids are ethanol, methanol and acetone. The preferred liquid is acetone in which Tween 80 ® has been dissolved to a concentration of 0.1% (weight volume). The nanospheres are washed with the said acetone solution before they are dried by rotational evaporation or freeze drying. They can also be kept for several months in the acetone solution.

The pharmacologically active substances can be incorporated with the carrier, on one hand by enclosure, in which case the pharmacologically active substance is mixed with the solution of carbohydrate and the magnetic material before the solution is emulsified and, on the other hand, by adsorption, in which case the pharmacologically active substance is mixed with the magnetic nanospheres in the aqueous phase. Alternatively, dried magnetic nanospheres may be added to a solution of pharmacologically active substance, in which case the substance can be coupled covalently to the carbohydrate matrix.

To enable the pharmacologically active substance to exert its effect, it must be releasable from the carrier material.

When the pharmacologically active substance is enclosed in and/or adsorbed to the crystallized carbohydrate matrix, release is effected by a combination of diffusion and erosion of the matrix, whereas in the case of a covalent coupling of the active substance, release is accomplished by degradation of the matrix.

It is also possible to vary the release rate of the pharmacologically active substance by cross-linking the matrix after crystallization. The tighter the matrix is cross-linked, the longer are the release times. Different types of cross-linking agents can be used, depending upon whether or not water is present at the cross-linkage. In aqueous environment, it is possible to use, inter alia, divinyl sulphone, epibromohydrin or BrCN. In the anhydrous phase, it is possible to activate with tresyl reagent, followed by cross-linking with a diamine.

The invention will now be described in more detail with reference to the following Examples which merely serve to illustrate the invention, not to restrict it.

EXAMPLE 1

0.2 g starch were dissolved in 1.0 ml formamide by heating to about 60° C. The clear solution was allowed to cool to room temperature, whereupon 70 mg magnetite particles (Ferrofluid Corp., Nashua, N.H., USA) were admixed to the starch solution. The solution was transferred to a 100 ml beaker containing 50 ml xylene/$CHCl_3$ (4:1) in which the emulsifiers Pluronic F-68 ® and Pluronic L-35 ® had been dissolved, both of which had a concentration of 2.5% (weight volume). The mixture was emulsified ultrasonically (Ultrasonic 350 G, 350 watt) for 1 min., whereupon the resulting emulsion was transferred to 400 ml acetone in which the emulsifier Tween 80 ® had been dissolved to a concentration of 0.1% (weight volume). Transfer of the emulsion to the acetone-Tween 80 ® solution was effected by pouring the emulsion in the form of a fine stream into the acetone under stirring at a rate of about 1000 r/min. The crystallized magnetic nanospheres were washed 4 times more with the said acetone solution, whereafter they were dried under rotational evaporation or freeze drying or, alternatively, were kept in the acetone solution.

EXAMPLE 2

Example 1 was repeated, but with the difference that instead of 70 mg magnetite particles 100 μl of water-based "Ferrofluid" were admixed to the starch solution (Catalogue No. A-01, 400 gauss from Ferrofluid Corp., Nashua, N.H., USA).

EXAMPLE 3

Example 1 was repeated, but with the difference that 140 mg magnetite particles were admixed to the starch solution instead of 70 mg.

EXAMPLE 4

Example 1 was repeated, but with the difference that maize oil alone was used instead of xylene/$CHCl_3$ (4:1) with the emulsifiers Pluronic F-68 ® and Pluronic L-35 ®.

EXAMPLE 5

Example 1 was repeated, but with the difference that the starch was crystallized in ethanol with the addition of 1 g Tween 80 ® per liter of ethanol, instead of acetone.

EXAMPLE 6

Example 1 was repeated, but with the difference that 0.45 g starch was dissolved in 0.1 ml DMSO instead of 0.2 g in formamide.

EXAMPLE 7

Example 1 was repeated, but with the difference that 0.4 g dextran (molecular weight 40,000 from Pharmacia AB) was dissolved in 1.00 ml water instead of 0.2 g starch in formamide.

EXAMPLE 8

Example 1 was repeated, but with the difference that 1.5 g lactose was dissolved in 1 ml water, and that the lactose solution was emulsified in oil.

EXAMPLE 9

Example 1 was repeated, with the difference that 1.5 g maltose was dissolved in 1 ml water, and that the maltose solution was emulsified in oil.

EXAMPLE 10

Example 1 was repeated, with the difference that 2.5 g glucose were dissolved in 1 ml water, and that the glucose solution was emulsified in oil.

EXAMPLE 11

The magnetic nanospheres obtained in any one of Examples 1-10 were mixed with $^3$H-vincristine, whereupon $^3$H-vincristine released by diffusion from the nanospheres was measured in vitro in a 0.1M Na-phosphate buffer at pH 7.5. After an initially high diffusion from the nanosphere, a relatively uniform leakage was obtained, and after 4 hours 30% of the added amount of $^3$H-vincristine were still adsorbed to the nanospheres.

EXAMPLE 12

1 g of a 50% (weight volume) aqueous solution of dextran having a molecular weight of 40,000 was mixed with 70 mg magnetite particles and 100 μl of an ovalbumin solution containing 100 mg ovalbumin/ml water. 5 μl $^{125}$I-labelled ovalbumin had previously been added to the latter solution.

The dextran-ovalbumin solution was suspended in 25 ml vegetable oil in a 100 ml beaker and cooled to +4° C. The mixture was emulsified ultrasonically for 1 min., whereupon the emulsion was poured into 200 ml acetone in which the emulsifier Tween 80 ® had been dissolved to a concentration of 0.1% (weight volume). While the emulsion was being carefully poured into the acetone solution, the latter was stirred at a rate of about 1000 r/min. The resulting dextran spheres stabilized by crystallization and enclosing ovalbumin and magnetite were washed 4 times more with the said acetone solution, whereupon they were air-dried.

Normally, such an experiment gives a yield of about 250 mg spheres where 60-70% of ovalbumin added are enclosed in the carbohydrate matrix.

EXAMPLE 13

Example 1 was repeated, but with the difference that interferon was used instead of ovalbumin.

EXAMPLE 14

Example 1 was repeated, but with the difference that plasmin was used instead of ovalbumin.

EXAMPLE 15

The nanospheres produced in Example 1 were used for covalently bonding high-molecular substances of the protein type. 1 ml nanospheres was activated with 200 μl epibromohydrin for 4 hours in 10 ml 0.1M NaOH. After washing, $^{125}$I-myoglobin was added and allowed to couple overnight. Unbonded myoglobin was washed off with 1 mM HCl, 0.3M NaCl and 0.1M NaHCO$_3$, pH 9.5, whereupon the activity was determined. 0.7 mg myoglobin had been covalently coupled to the starch matrix.

Under the action of alpha-amylase in a concentration which was 100 times higher than in normal human serum, about 30% of coupled $^{125}$I-myoglobin had been released from the matrix after 24 hours at room temperature and in 0.1M Na-phosphate buffer, pH 7.5.

In vivo experiment

The magnetic nanospheres obtained in Example 1 were used for in vivo testing on rats.

To test the half-life in the circulation, the rat was anaesthetised with 5% chloral injected intraperitoneally, whereupon v. femoralis and the central tail artery were both catheterised cranially. The radioactively labelled magnetic nanospheres were injected via v. femoralis, and blood samples were taken via the tail artery at predetermined time intervals, whereupon the circulating amount of magnetic nanospheres was determined. The half-life obtained showed that the majority of the number of magnetic nanospheres had such a long half-life in the circulation that they can be concentrated in an organ of the body to an extent sufficient to attain therapeutical concentration of the transported, pharmaceutically active preparation.

In another experiment, the rat was killed after a predetermined time, whereupon the amount of magnetic nanospheres in different organs, inter alia the brain, was determined. This experiment was repeated, but this time with the rat's head positioned in a magnetic field of 1 Tesla, and a marked increase of the radioactivity in the brain was observed.

We claim:

1. A nanosphere or nanoparticle for intravascular administration, which is magnetically responsive and biologically degradable and which is made up of a matrix in which a magnetic material is enclosed, characterized in that said nanosphere or nanoparticle has an average diameter which does not exceed 1500 nm, and circulates in the vascular system after administration thereto, said matrix comprising a hydrophillic, crystalline carbohydrate.

2. A nanosphere or a nanoparticle as claimed in claim 1, characterised in that the magnetic material is present in the form of particles or a colloid.

3. A nanosphere or a nanoparticle as claimed in claim 2, characterised in that the magnetic material consists of magnetite particles having an average diameter of 1-1000 nm, preferably 10-20 nm.

4. A nanosphere or a nanoparticle as claimed in one or more of claims 1, 2, or 3, characterised in that the crystalline carbohydrate is glucose, maltose or lactose.

5. A nanosphere or a nanoparticle as claimed in one or more of claims 1, 2, or 3, characterised in that the crystalline carbohydrate is a carbohydrate polymer, preferably with alpha(1-4) bonds between the carbohydrates comprised by the polymer.

6. A nanosphere or a nanoparticle as claimed in claim 5, characterised in that the carbohydrate polymer is starch, glycogen, pullullan or a derivative thereof.

7. A nanosphere or a nanoparticle as claimed in claim 5, characterised in that the carbohydrate polymer is dextran or a derivative thereof.

8. Use of the nanosphere or the nanoparticle as claimed in claim 1 for transport and concentration of pharmacologically active substances in biological systems, preferably animal systems.

* * * * *